United States Patent [19]

Wasleski et al.

[11] Patent Number: 5,502,190
[45] Date of Patent: Mar. 26, 1996

[54] PROCESS FOR THE PRODUCTION OF DIALKYL PYRIMIDYLPHOSPHATES

[75] Inventors: Daniel M. Wasleski, Raytown; David T. Erdman, Kansas City, both of Mo.; Peter E. Newallis, Leawood, Kans.

[73] Assignee: Bayer Corporation, Pittsburgh, Pa.

[21] Appl. No.: 151,322

[22] Filed: Nov. 12, 1993

[51] Int. Cl.$^6$ ............................................. C07F 9/6512
[52] U.S. Cl. ........................ 544/243; 544/298; 548/335.1
[58] Field of Search ............................... 544/243, 337; 546/25

[56] References Cited

U.S. PATENT DOCUMENTS

| | | | |
|---|---|---|---|
| 4,094,873 | 6/1978 | Kroposki et al. | 544/243 |
| 4,147,866 | 4/1979 | Freedman et al. | 544/243 |
| 4,357,328 | 11/1982 | Pawloski | 544/244 |
| 4,429,125 | 1/1984 | Reifshneider | 544/243 |
| 4,729,987 | 3/1988 | Reifschneider | 514/86 |

FOREIGN PATENT DOCUMENTS 277292  8/1988  European Pat. Off. .

*Primary Examiner*—Emily Bernhardt
*Attorney, Agent, or Firm*—Joseph C. Gil; Lyndanne M. Whalen; Godfried R. Akorli

[57] ABSTRACT

O,O-dialkyl pyrimidylphosphates are made by reacting an O,O-dialkyl phosphorohalothioate with a 5-hydroxypyrimidine in the presence of an imidazole phase transfer catalyst, an aromatic solvent and an alkali metal hydroxide at a pH of from about 8 to about 12 and a temperature of up to about 70° C. The products of this process are obtained in high yield. These compounds are useful as pesticides and insecticides.

15 Claims, No Drawings

PROCESS FOR THE PRODUCTION OF DIALKYL PYRIMIDYLPHOSPHATES

BACKGROUND OF THE INVENTION

The present invention relates to a process for the production of O,O-dialkyl pyrimidylphosphates.

Pyrimidylphosphates are known to be useful in the control of soil pests or insects such as corn rootworm, thrips, leafhoppers, and nematodes when applied to the soil of crops such as corn, sorghum, cotton, and sugar beets.

Processes for making these pesticides are also known. U.S. Pat. No. 4,094,873, for example, discloses a process in which an alkali metal phenoxide, pyridinoxide or pyrimidinoxide is reacted with an O,O-dialkyl-phosphoro-chloridothioate or O-alkyl phenylphosphonochloridothioate in the presence of a catalyst mixture under alkaline conditions in a liquid reaction medium. The catalyst mixture is made up of a quaternary ammonium salt and a diazole.

U.S. Pat. No. 4,147,866 also discloses a process in which an alkali metal phenoxide, pyridinoxide or pyrimidinoxide is reacted with an O,O-dialkyl phosphorochloridothioate in the presence of a catalyst mixture under alkaline conditions in a liquid reaction medium. The catalysts used in this process are a quaternary ammonium salt and a sterically unhindered, nucleophilic, tertiary amine. U.S. Pat. No. 4,147,866 also teaches that use of either the tertiary amine or the quaternary ammonium catalyst alone results in low yields, high amounts of unwanted by-products and expensive, difficult purification steps.

However, the use of two catalysts in the processes disclosed in U.S. Pat. No. 4,094,873 and 4,147,866 is disadvantageous because the cost of raw materials and product purification is increased.

U.S. Pat. No. 4,429,125 discloses a process for the production of phosphorus esters of 5-pyrimidinols in which a 5-pyrimidinol is reacted with a phosphorochloridothioate in an inert organic liquid in the presence of an acid binding agent or acceptor. The acid binding agent or acceptor is selected from alkali carbonates, alkali hydroxides and alcoholates such as sodium carbonate, potassium carbonate, sodium or potassium methoxide, sodium or potassium ethoxide, and amines. No phase transfer catalyst is included in the reaction mixture.

U.S. Pat. No. 4,729,987 also discloses a process in which a 5-pyrimidinol represented by a given formula is reacted with a phosphorochloridothioate in an inert organic liquid and an acid binding agent or acceptor at a temperature of from about 0° to about 100° C. No phase transfer catalyst is included in the reaction mixture.

Published European Patent Application 277,292 discloses a process for producing O-pyrimidinyl phosphorus compounds in which an aqueous solution of a salt of a pyrimidine is reacted with a phosphorus ester in the presence of a phase transfer catalyst without added organic solvent. This disclosure teaches that low yields are to be expected when an organic solvent such as toluene is used as the reaction medium.

SUMMARY OF THE INVENTION

It is an object of the present invention to provide an improved process for the production of O,O-dialkyl pyrimidylphosphates.

It is also an object of the present invention to provide a process for the production of O,O-dialkyl pyrimidylphosphates in which only a single phase transfer catalyst is employed.

It is another object of the present invention to provide a process for the production of O,O-dialkyl pyrimidylphosphates in which the phase transfer catalyst is effective even when the reaction is carried out in an aromatic solvent.

These and other objects which will be apparent to those skilled in the art are accomplished by reacting an O,O-dialkyl phosphorohalothioate with a 5-hydroxypyrimidine in the presence of a phase transfer catalyst, an aromatic solvent and an alkali metal hydroxide at a pH of from about 8 to about 12 and a temperature of up to 70° C. The phase transfer catalyst must be an imidazole. The product O,O-dialkyl pyrimidylphosphate may be recovered from the reaction mixture by adding water to the reaction mixture with agitation to cause the formation of an aqueous and an organic phase. The organic and aqueous phases may then be separated and the organic solvent removed from the organic phase by, e.g., steam stripping.

DETAILED DESCRIPTION OF THE PREFERRED EMBODIMENTS OF THE INVENTION

The present invention relates to a process in which an O,O-dialkyl phosphorohalothioate is reacted with a 5-hydroxypyrimidine in the presence of an imidazole phase transfer catalyst, an aromatic solvent and an alkali metal hydroxide. This reaction is carried out at a pH of from about 8 to about 12 and a temperature of up to 70° C.

The O,O-dialkyl phosphorohalothioates useful in the process of the present invention are known. Examples of such compounds include those represented by the formula

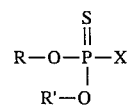

in which

R and R' each represent a lower alkyl group, preferably an alkyl group having from 1 to 4 carbon atoms, and X represents a halogen atom, preferably chloride.

Preferred O,O-dialkyl phosphorohalothioates include: O-ethyl-O-(1-methyl-ethyl)phosphorochloridothioate; O,O-diethyl phosphorochloridothioate; O,O-dimethylphosphorochloridothioate; and O,O-di-(1-methylethyl)phosphorochloridothioate. The O,O-dialkyl phosphorohalothioate is generally dispersed in the aromatic solvent before being brought into contact with the 5-hydroxypyrmidine.

The 5-hydroxypyrimidines useful in the process of the present invention include any of the known 5-hydroxypyrimidines, particularly the 2-(alkyl)-5-hydroxypyrimidines represented by the formula

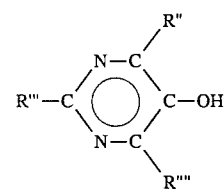

in which

R" represents hydrogen, methyl or an alkylthio group having from 1 to 2 carbon atoms;

R'" represents hydrogen, an alkyl group having from 1 to 8 carbon atoms, an alkylthiomethyl group, an alkylsulfinylmethyl group or an alkylsulfonylmethyl group with alkyl meaning from 1 to 4 carbon atoms, a phenyl group, a phenylthio group, an alkylthio group having from 1 to 4 carbon atoms, an alkylsulfinyl group having from 1 to 4 carbon atoms, an alkylsulfonyl group having from 1 to 4 carbon atoms, or an alkylthioethylthio group having from 1 to 2 carbon atoms in the alkyl group; and R"" represents hydrogen or a methyl group.

Particularly preferred 5-hydroxypyrimidines include: 2-(1,1-dimethyl-ethyl)- 5-hydroxypyrimidine; 2-(1-methylethyl)-5-hydroxypyrimidine; 2-ethyl-5-hydroxypyrimidine; and 2-((1-methylethyl)thio)- 5-hydroxypyrimidine.

The phase transfer catalyst used in the process of the present invention must be an imidazole. Any of the known imidazoles may be used. Such compounds are represented by the formula:

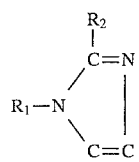

in which $R_1$ represents a lower alkyl group having from 1 to 6 carbon atoms, preferably methyl or ethyl, most preferably methyl;

and $R_2$ represents hydrogen or a lower alkyl group having from 1 to 6 carbon atoms, preferably a methyl or ethyl group, most preferably a methyl group.

Examples of suitable imidazoles include: 1-methylimidazole, 1-ethylimidazole, 1-propylimidazole, 1-hexylimidazole and 1,2-dimethylimidazole.

The aromatic solvents useful in the process of the present invention include any of the known and commonly used aromatic organic solvents. Specific examples of suitable solvents include: toluene, benzene, xylene, mesitylene, cumene, ethylbenzene and chlorobenzene.

The process of the present invention is carried out at a pH of from about 8 to about 12 in the presence of an alkali metal hydroxide. Any of the alkali metal hydroxides may be used but sodium hydroxide is particularly preferred.

The reaction which occurs in the process of the present invention is carried out at a temperature of up to 70° C., preferably at a temperature of from about 30° to about 60° C., most preferably at a temperature of about 45° C.

The reaction components are generally used in amounts such that at least 0.5 moles of O,O-dialkyl phosphorohalothioate (concentration in aromatic solvent such as toluene from about 10 to about 90%, preferably from about 50 to about 80%) are present for each mole of 5-hydroxypyrimidine, preferably from about 0.97 to about 0.95 moles of O,O-dialkyl phosphorohalothioate per mole of 5-hydroxypyrimidine. The imidazole phase transfer catalyst is generally used in an amount of from about 1 g to about 20 g per mole of 5-hydroxypyrimidine. The alkali metal hydroxide is generally used in an amount sufficient to maintain the pH of the reaction mixture between about 8 and about 12. Generally, from about 1 to about 1.1 moles of alkali metal hydroxide per mole of 5-hydroxypyrimidine are present in the reaction mixture. The alkali metal hydroxide is generally used in the form of an aqueous solution having a concentration of from about 10 to about 50% by weight.

After the reaction between the O,O-dialkyl phosphorohalothioate and the 5-hydroxypyrimidine has been substantially completed, the product O,O-dialkyl pyrimidylphosphate may be recovered by, for example, a phase separation process. In a phase separation process, water is added to the reaction mixture with agitation. The resultant mixture is allowed to settle until two distinct phases are formed. The organic phase which includes the product to be recovered is separated from the aqueous phase and then treated (e.g., steam stripped) to remove the organic solvent. The O,O-dialkyl pyrimidylphosphate remains.

The process of the present invention produces the desired O,O-dialkyl pyrimidylphosphate in yields of at least 89% in reaction times as short as 3 hours. Typical reaction times range from about 3 to about 6 hours depending on the specific reaction conditions.

Having thus described our invention, the following examples are given as being illustrative thereof. All pads and percentages given in these examples are parts by weight and percentages by weight, unless otherwise indicated.

EXAMPLES

EXAMPLES 1–9

80.0 g (0.5 moles) of 25% sodium hydroxide were added dropwise to a mixture of 135.0 g (0.5 moles) of O-ethyl-O-(1-methylethyl)phosphoro-chloridothioate (75% in toluene), 79.0 g (0.52 moles) of 2-(1,1-dimethylethyl)-5-hydroxypyrimidine and 1 g of 1-methyl imidazole at 45° C. The sodium hydroxide was added at a rate sufficient to maintain the pH of the reaction mixture between 8 and 10. The reaction mixture was subsequently stirred at 45° C. until the unreacted phosphorochloridothioate was less than 0.5% as determined by gas chromatography. The mixture was then cooled to 25° C. and 50 ml of water were added. The resultant mixture was agitated for 15 minutes and allowed to stand until the organic and aqueous layers separated. The layers were separated and the organic layer was steam stripped to remove any toluene present. O-[2-(1,1-dimethylethyl)-5-pyrimidinyl]-O-ethyl-O-(1-methylethyl) phosphorothioate was recovered. The g/mole of 1-methyl imidazole, pH, reaction times and yields are reported in Table 1.

TABLE 1

| EXAMPLE | CATALYST (g/mole*) | pH | TEMP. (°C.) | TIME (HRS) | YIELD |
| --- | --- | --- | --- | --- | --- |
| 1 | 1 | 10 | 35 | 13 | 90.1% |
| 2 | 1 | 8 | 35 | 11 | 90.2% |
| 3 | 2 | 10 | 35 | 5.5 | 91.3% |
| 4 | 2 | 8 | 35 | 5 | 89.1% |
| 5 | 4 | 10 | 35 | 4 | 89.8% |
| 6 | 4 | 8 | 35 | 3.5 | 90.2% |
| 7 | 2 | 8 | 45 | 3 | 90.6% |
| 8 | 2 | 8 | 45 | 4 | 92.3% |
| 9 | 1 | 8 | 65 | 3 | 89.0% |

*grams of catalyst per mole of 2-(1,1-dimethylethyl)-5-hydroxypyrimidine.

EXAMPLES 10–13

A solution of O-ethyl-O-(1-methylethyl)-phosphorochloridothioate (75% in toluene) was added dropwise over a period of two hours to a mixture of 80.0 g (0.5 moles) of 25% sodium hydroxide, 79.0 g (0.52 moles) of 2-(1,1-dimethylethyl)-5-hydroxypyrimidine and 1-methylimidazole (in the relative amount indicated in Table 2) at the pH and temperature indicated in Table 2. The reaction mixture was stirred at 45° C. until the unreacted phosphorochloridothioate was less than 0.5% as determined by gas chromatography. The reaction mixture was then cooled to 25° C. and 50 ml of water were added. The mixture was then agitated for 15 minutes and allowed to settle. The organic and aqueous layers separated and the organic layer was then steam stripped to remove toluene. O-[2-(1,1-dimethylethyl)-5-pyrimidinyl]-O-ethyl-O-(1-methylethyl)phosphorothioate was recovered in the yield reported in Table 2.

TABLE 2

| EXAMPLE | CATALYST (g/mole*) | pH | TEMP. °C. | TIME (hrs.) | Yield |
|---|---|---|---|---|---|
| 10 | 1 | 8 | 35 | 9 | 88.7% |
| 11 | 1 | 8 | 45 | 11 | 90.2% |
| 12 | 1 | 8 | 55 | 6 | 91.8% |
| 13 | 2 | 8 | 35 | 17 | 89.6% |

*grams of 1-methyl imidazole per mole of 2-(1,1-dimethylethyl)-5-hydroxypyrimidine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an O,O-dialkyl pyrimidylphosphate comprising reacting components consisting essentially of:

a) an O,O-dialkyl phosphorohalothioate with
  b) a 5-hydroxypyrimidine which is of the formula

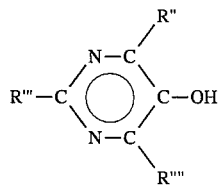

in which
  R" represents hydrogen, methyl or an alkylthio group having from 1 to 2 carbon atoms;
  R'" represents hydrogen, an alkyl group having from 1 to 8 carbon atoms, an alkylthiomethyl group, an alkylsulfinylmethyl group or an alkylsulfonylmethyl group with alkyl meaning from 1 to 4 carbon atoms, a phenyl group, a phenylthio group, an alkylthio group having from 1 to 4 carbon atoms, an alkylsulfinyl group having from 1 to 4 carbon atoms, an alkylsulfonyl group having from 1 to 4 carbon atoms, or an alkylthioethylthio group having from 1 to 2 carbon atoms in the alkyl group; and
  R"" represents hydrogen or a methyl group in the presence of c) a phase transfer catalyst consisting essentially of an imidazole,
  d) an aromatic solvent, and
  e) an alkali metal hydroxide
at a pH of from about 8 to about 12 and a temperature of up to about 70° C.

2. The process of claim 1 in which the alkyl pyrimidylphosphate is recovered from the reaction mixture by
  a) adding water to the reaction mixture with agitation, p1
  b) separating the organic and aqueous layers
  c) stripping the organic layer separated in b) of the organic solvent present therein and
  d) recovering the O,O-dialkyl pyrimidylphosphate.

3. The process of claim 1 in which the reaction is carried out at a temperature of from about 30° to about 60° C.

4. The process of claim 1 in which the reaction is carried out at a temperature of about 45° C.

5. The process of claim 1 in which the reaction is carried out at a pH of about 8.

6. The process of claim 1 in which the O,O-dialkyl phosphorohalothioate has alkyl groups with from 1 to 4 carbon atoms.

7. The process of claim 1 in which the O,O-dialkyl phosphorochloridothioate is O-ethyl-O-(1-methylethyl) phosphorochloridothioate.

8. The process of claim 7 in which the 5-hydroxypyrimidine is 2-(1,1-dimethylethyl)-5-hydroxypyrimidine.

9. The process of claim 1 in which the 5-hydroxypyrimidine is a 2-(alkyl)-5-hydroxypyrimidine.

10. The process of claim 1 in which the 5-hydroxypyrimidine is 2-(1,1-dimethylethyl)-5-hydroxypyrimidine.

11. The process of claim 1 in which the imidazole is selected from the group consisting of 1-methyl imidazole and 1,2-dimethylimidazole.

12. The process of claim 1 in which the organic solvent is selected from the group consisting of toluene, benzene, xylene, cumene, ethylbenzene, mesitylene, and chlorobenzene.

13. The process of claim 1 in which the alkali metal hydroxide is sodium hydroxide.

14. The process of claim 1 in which the organic solvent is removed from the organic phase by steam stripping.

15. The process of claim 1 in which the imidazole is 1-methylimidazole, the organic solvent is toluene and the alkali metal hydroxide is sodium hydroxide.

* * * * *